United States Patent
Sekido et al.

(10) Patent No.: US 11,046,061 B2
(45) Date of Patent: Jun. 29, 2021

(54) LAMINATE

(71) Applicant: Toray Industries, Inc., Tokyo (JP)

(72) Inventors: Yuki Sekido, Otsu (JP); Motonori Hochi, Otsu (JP); Mao Fujii, Otsu (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 16/087,423

(22) PCT Filed: Mar. 23, 2017

(86) PCT No.: PCT/JP2017/011563
§ 371 (c)(1),
(2) Date: Sep. 21, 2018

(87) PCT Pub. No.: WO2017/164264
PCT Pub. Date: Sep. 28, 2017

(65) Prior Publication Data
US 2019/0099990 A1  Apr. 4, 2019

(30) Foreign Application Priority Data

Mar. 23, 2016 (JP) .............................. JP2016-057786

(51) Int. Cl.
*B32B 27/12* (2006.01)
*B32B 5/02* (2006.01)
(Continued)

(52) U.S. Cl.
CPC .............. *B32B 27/12* (2013.01); *A61L 15/24* (2013.01); *A61L 15/26* (2013.01); *A61L 15/28* (2013.01);
(Continued)

(58) Field of Classification Search
CPC ........... B32B 5/02; B32B 27/12; B32B 27/36; A61L 15/28
See application file for complete search history.

(56) References Cited

U.S. PATENT DOCUMENTS

2008/0241203 A1  10/2008 Morinaga et al.
2011/0259518 A1* 10/2011 Tojo .......................... B32B 5/02
156/308.6
(Continued)

FOREIGN PATENT DOCUMENTS

JP  2003-153999 A  5/2003
JP  2015-039870 A  3/2015
(Continued)

*Primary Examiner* — Frank J Vineis
*Assistant Examiner* — Nicole T Gugliotta
(74) *Attorney, Agent, or Firm* — DLA Piper LLP (US)

(57) ABSTRACT

A laminate has better handling properties achieved when it is attached to an adherend and which allows the solubility irregularity of the water-soluble material layer to be suppressed. The laminate includes: a 10 to 500 nm thick biodegradable material layer containing an aliphatic polyester and a water-soluble material layer disposed on at least one side of the biodegradable material layer, in which the water-soluble material layer is constituted of a 1 to 20 μm thick first layer containing a water-soluble polymer (a), a 10 μm to 10 mm thick fabric structure containing a water-soluble polymer (b), and a 1 to 20 μm thick second layer containing a water-soluble polymer (c), which are layered in this order from the biodegradable material layer side.

9 Claims, 1 Drawing Sheet

(51) Int. Cl.
    B32B 7/12      (2006.01)
    B32B 27/30     (2006.01)
    B32B 27/36     (2006.01)
    B32B 27/40     (2006.01)
    B32B 9/04      (2006.01)
    B32B 23/10     (2006.01)
    B32B 27/28     (2006.01)
    B32B 9/02      (2006.01)
    B32B 23/08     (2006.01)
    B32B 23/04     (2006.01)
    B32B 27/08     (2006.01)
    A61L 15/58     (2006.01)
    A61L 15/24     (2006.01)
    A61L 15/26     (2006.01)
    A61L 15/28     (2006.01)
    A61L 31/12     (2006.01)
    A61L 31/04     (2006.01)
    A61L 31/06     (2006.01)
    A61L 31/14     (2006.01)
(52) U.S. Cl.
    CPC ............. *A61L 15/58* (2013.01); *B32B 5/02* (2013.01); *B32B 5/022* (2013.01); *B32B 7/12* (2013.01); *B32B 27/306* (2013.01); *B32B 27/36* (2013.01); *A61L 31/04* (2013.01); *A61L 31/06* (2013.01); *A61L 31/12* (2013.01); *A61L 2300/604* (2013.01); *B32B 2255/10* (2013.01); *B32B 2255/26* (2013.01); *B32B 2307/7163* (2013.01); *B32B 2307/7166* (2013.01); *B32B 2535/00* (2013.01)

(56) References Cited

U.S. PATENT DOCUMENTS

| | | | |
|---|---|---|---|
| 2013/0122069 A1* | 5/2013 | Tojo | A61K 8/0208 424/401 |
| 2013/0142852 A1* | 6/2013 | Tojo | A61K 8/0208 424/401 |
| 2017/0072669 A1 | 3/2017 | Sekido et al. | |

FOREIGN PATENT DOCUMENTS

| | | |
|---|---|---|
| WO | 2005/094915 A1 | 10/2005 |
| WO | 2011/081162 A1 | 7/2011 |
| WO | 2014/141983 A1 | 9/2014 |
| WO | 2015/152204 A1 | 10/2015 |
| WO | 2015/194616 A1 | 12/2015 |

* cited by examiner

LAMINATE

TECHNICAL FIELD

This disclosure relates to laminates.

BACKGROUND

Surgical operations typified by abdominal surgery, orthopedic surgery, neurosurgery and the like have a problem of adhesion between internal organs as one of the postoperative complications. This is because there may occur an adhesion phenomenon, i.e., coaptation between internal organ tissues that originally should not be coapted, in the process of self-healing in the wound healing of normal tissues that have been damaged by drying and oxidation in a surgery and have been sutured. It is said that there is a high probability of adhesion occurring in surgical operations, and the adhesion may lead to complications that cause serious pathological conditions such as pain, ileus, and infertility.

Once the adhesion forms, it is difficult to treat it by medication. In some cases, ileus occurs owing to an adhesion several years after a surgery. It is believed that adhesion treatment can be carried out only by adhesiotomy in which an adhesion is ablated by performing a surgical operation again, and, in the surgical operation, it is important to prevent adhesion and prevent delay of healing.

As materials having an adhesion prevention effect and a healing delay prevention effect, adhesion prevention materials are conventionally known in which gelatin or collagen expected to be bioabsorbable is used to physically separate internal organ tissues.

In addition, adhesion prevention films need to indwell in the body after surgery and preferably degrade after the surgical site is healed. It is accordingly necessary that they have a low risk of infectious disease, safety for the living body, and high in vivo degradability and absorbability. As such an adhesion prevention materials, a highly bioabsorbable adhesion prevention film using sodium alginate has been reported, which is a water-containing polysaccharide having excellent preservation stability and thermal stability or the like (JP 2003-153999 A).

Further, as adhesion prevention films, adhesion prevention materials are known which are provided with a plurality of functions by having a plurality of layers having a specific function. Adhesion prevention films are reported which are combinations of a biodegradable base material layer formed of a biodegradable and bioabsorbable polymer such as collagen, polylactic acid, or polyglycolic acid having good biocompatibility and degraded and absorbed in a certain period of time, and an adhesion prevention layer formed of a polymer such as collagen, gelatin or hyaluronic acid having an adhesion prevention effect, and which can prevent adhesion also around the damaged or defective end portions of a tissue (WO 2005/094915).

In addition, there is a report on a laminate in which a fabric structure containing a water-soluble polymer and a polylactic acid polymer having a thickness in nanometers are layered such that the thickness of the fabric structure affords excellent handling properties when the laminate is attached to an adherend and such that, after the laminate is attached to the adherend, applying some water to the fabric structure allows only the layer containing the polylactic acid polymer to be left on the tissue; and in which providing the layer containing a water-soluble polymer between the polylactic acid polymer and the fabric structure enhances adhesiveness between the polylactic acid polymer and the fabric structure (WO 2015/194616).

JP '999 discloses that the adhesion prevention material described therein has high bioabsorbability because polysaccharide is used as the material. There is a problem, however, in that the adhesion prevention material formed of polysaccharide has insufficient strength and makes it difficult for an operator to put in a suture. In addition, the too high bioabsorbability conversely makes it difficult to maintain the sutured condition for a certain period of time.

WO '915 discloses that the adhesion prevention material described therein has a structure in which a biodegradable base material layer and an adhesion prevention layer are combined to prevent adhesion while the defective portions between tissues are retained. However, WO '915 does not describe whether the handling properties of the adhesion prevention material thereof have been enhanced to attach the adhesion prevention material to the surface of a tissue, nor describe any specific configuration for solving the question.

On the other hand, WO '616 discloses that the laminate described therein has its adhesiveness increased and its handling properties enhanced by having a structure in which a polylactic acid polymer having a thickness in nanometers and a fabric structure containing a water-soluble polymer are layered having, inbetween, a layer containing a water-soluble polymer, but the fabric structure containing a water-soluble polymer is exposed as the outermost layer, resulting in not only a possibility that the nonuniformity in the mass per unit area and the like of the fabric structure causes irregularity in the solubility after the attachment of the laminate, but also a possibility that the handling properties in attaching the laminate are decreased because the laminate will be easily dissolved if it is wetted by mistake when attached to an adherend.

It could therefore be helpful to provide a laminate having better handling properties achieved for attaching it to an adherend and that allows its solubility irregularity to be suppressed when attached to an adherend.

SUMMARY

We thus provide:
(1) A laminate including: a 10 to 500 nm thick biodegradable material layer containing an aliphatic polyester and a water-soluble material layer disposed on at least one side of the biodegradable material layer, in which the water-soluble material layer is constituted by a 1 to 20 μm thick first film containing a water-soluble polymer (a), a 10 μm to 10 mm thick fabric structure containing a water-soluble polymer (b), and a 1 to 20 μm thick second film containing a water-soluble polymer (c), which are layered in this order from the biodegradable material layer side.
(2) The laminate according to (1), in which the laminate is such that 5 seconds or more but less than 5 minutes is required from the time when water is dropped onto the surface of the second film to the time when the surface of the first film is dissolved, in which the surface of the first film is in contact with the biodegradable material layer.
(3) The laminate according to (1) or (2), having a piercing strength of 0.3 to 30 N.
(4) The laminate according to any one of (1) to (3), in which the biodegradable material layer has a thickness of 10 to 200 nm.
(5) The laminate according to any one of (1) to (4), in which the first film has a thickness of 2 to 10 μm.
(6) The laminate according to any one of (1) to (5), in which the second film has a thickness of 5 to 20 μm.

(7) The laminate according to any one of (1) to (6), in which the fabric structure has a thickness of 100 μm to 1 mm.
(8) The laminate according to any one of (1) to (7), in which the water-soluble polymer is pullulan or polyvinyl alcohol.
(9) The multilayer laminate according to any one of (1) to (8), in which the aliphatic polyester is a polylactic acid polymer.

Because the laminate has an outermost surface of a water-soluble material layer removable with moisture, which is a different layer from a fabric structure, the laminate can retain its shape to a certain degree over time and retain its handling properties, even if a small amount of moisture is applied to the laminate when the laminate is attached to an adherend. Also, after the laminate is attached to the adherend, the water-soluble material layer can be removed with moisture, whereby the thin film aliphatic polyester having excellent conformability, adhesiveness and coatability to the curved surface adherend can be left on the adherend. Hence, the laminate can be utilized suitably for medical supplies such as wound dressings and adhesion prevention materials and for topical materials for skin such as skin care products and adhesive bandages.

DETAILED DESCRIPTION

Figure 1:
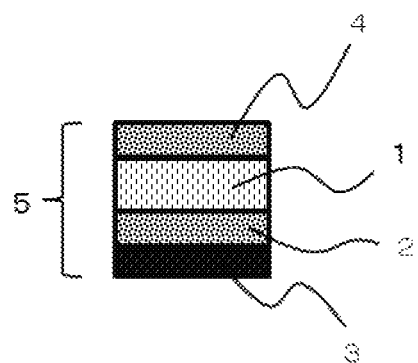
FIG. 1 is a schematic cross-sectional view depicting an example of the laminate.

Below, our laminates are described in detail together with examples thereof. As used herein, the term "film" refers to a structure having a two-dimensional expanse, for example, a sheet, a plate, a discontinuous film containing voids or the like.

The term "fabric structure" refers to a fabric aggregate, in which the fibers may be fixed or unfixed between each other.

The term "laminate" refers to a construct composed of a plurality of layers in which monolayer or multilayer films or monolayer or multilayer fabric structures or the like are layered.

Laminate

The laminate includes: a 10 nm to 500 nm thick biodegradable material layer containing an aliphatic polyester and a water-soluble material layer disposed on at least one side of the biodegradable material layer, in which the water-soluble material layer is constituted of a 1 μm to 20 μm thick first film containing a water-soluble polymer (a), a 10 μm to 10 mm thick fabric structure containing a water-soluble polymer (b), and a 1 μm to 20 μm thick second film containing a water-soluble polymer (c), layered in this order from the biodegradable material layer side.

With the laminate, the water-soluble material layer which has been rid of the 10 nm to 500 nm thick biodegradable material layer containing an aliphatic polyester preferably has water-solubility such that 5 seconds or more but less than 5 minutes is required from the time when water (about 0.04 ml) is dropped onto the second film to the time when the water reaches the surface of the first film. The phrase "water reaches the surface of the first film" means that the fabric structure has been dissolved and cannot retain the fabric shape because the fibers thereof have been dissolved.

The 5 seconds or more is preferable because it enables the laminate to be easily handled in the presence of moisture, blood and the like. When the laminate is used as a support for an adhesion prevention material, the time is more preferably 20 seconds or more, particularly preferably 1 minute or more, since a certain time is required before the laminate is attached to a tissue. On the other hand, the less than 5 minutes is preferable because the laminate can be promptly removed after it is attached to a tissue. Imparting long-time water resistance to the laminate can be achieved using, for example, a method in which the first film and the second film are made thick, a method in which the fabric structure is allowed to have higher mass per unit area or higher density, but in these cases, the laminate tends to give a rigid feeling. Because of this, preferably 3 minutes or less, particularly preferably 2 minutes or less, is required from the time when water is dropped onto the second film to the time when the water reaches the surface of the biodegradable material layer.

Biodegradable Material Layer Containing Aliphatic Polyester

The biodegradable material layer containing an aliphatic polyester refers to a biodegradable material layer structure containing at least an aliphatic polyester described below.

The above-mentioned aliphatic polyester is a polymer in which monomers having an ester group are polymerized by ester linkage but refers to a polyester containing no aromatic ring in the molecule, and specific examples thereof include polymers such as polylactic acid, polycaprolactone, polybutylene succinate, polyhydroxy butyrate and the like.

The thickness of the above-mentioned biodegradable material layer is 10 nm to 500 nm from the viewpoint of shape conformability to adherends, more preferably 10 nm to 200 nm, still more preferably 20 nm to 200 nm. A thickness of less than 10 nm may make it difficult to retain the shape, and a thickness of more than 500 nm may cause wrinkles in the laminate when it is attached to an adherend.

The aliphatic polyester has a weight-average molecular weight of preferably 30,000 to 400,000, more preferably 50,000 to 400,000, still more preferably 80,000 to 400,000, still more preferably 100,000 to 500,000. As used herein, the term "weight-average molecular weight" refers to a molecular weight based on measurement by gel permeation chromatography (GPC) with a chloroform solvent and calculated using a polymethyl methacrylate (PMMA) conversion method. Using the aliphatic polyester having a weight-average molecular weight of 30,000 to 400,000 enables the biodegradable material layer containing the aliphatic polyester to have excellent mechanical properties.

The biodegradable material layer may contain 2 mass % or more but 20 mass % or less of an impact resistance modifier with respect to 100 mass % of the whole biodegradable material layer for the purpose of enhancing the mechanical strength. It is preferably 2.5 mass % or more but 15 mass % or less. The more the impact resistance modifier content is, the more enhanced the impact resistance modification effect is, but in some cases, the mechanical strength is not significantly enhanced even if the content is more than 20 mass %.

The biodegradable material layer may contain 30 mass % or less of various additives with respect to 100 mass % of the whole biodegradable material layer to the extent that the desired effects are not impaired. Examples of usable additives include antioxidants, weathering agents, heat stabilizers, lubricants, nucleating agents, ultraviolet absorbers, coloring agents and the like. The lower limit of the additives content is not limited to a particular value, and it is no problem if the content is 0 mass % with respect to 100 mass % of the whole layer (C) containing an aliphatic polyester. The biodegradable material layer may contain 20 mass % or less of inorganic or organic particles with respect to 100 mass % of the whole biodegradable material layer to the extent that the transparency is not impaired. Examples thereof include: particles of calcium carbonate, titanium oxide, silicon oxide, calcium fluoride, lithium fluoride, alumina, barium sulfate, zirconia, calcium phosphate, and cross-linked polystyrene; metal nanoparticles; and the like. The lower limit of the inorganic or organic particles content is not limited to a particular value, and it is no problem if the content is 0 mass % with respect to 100 mass % of the whole biodegradable material layer.

In addition, to the extent that the desired effects are not impaired, a bioabsorbable material layer containing gelatin, collagen, hyaluronic acid, chitosan, synthetic polypeptide and the like may further be formed on at least one side of the biodegradable material layer. When the side of the biodegradable material layer is the side on which no water-soluble material layer is layered, the adhesiveness to an adherend may be enhanced because the bioabsorbable material layer has water absorbability. In addition, when the side of the biodegradable material layer is the side on which a water-soluble material layer is layered, forming a bioabsorbable material layer between the biodegradable material layer and the water-soluble material layer makes it possible to use the bioabsorbable material layer to adjust the adhesive strength between the biodegradable material layer and the water-soluble material layer.

In addition, a reinforcing layer may further be formed on that side of the biodegradable material layer on which the water-soluble material layer is not layered, for the purpose of enhancing the form stability and dimensional stability of the fabric structure. Specific examples of usable reinforcing layers include woven fabrics, knitted fabrics, nonwoven fabrics (including paper), plastic films, metal thin films and the like.

In that the biodegradable material layer containing an aliphatic polyester has an invisible attaching face because the layer is transparent, it can be not only used for surgical operations but also attached to skin and used as an adhesive bandage.

Furthermore, the biodegradable material layer containing an aliphatic polyester can be used as a base material, whereby various pharmaceuticals can be supported or made controlled release and also used in a drug delivery system.

Polylactic Acid Polymers

The above-mentioned aliphatic polyester is more preferably a polylactic acid polymer.

The polylactic acid polymers refers to a polymer containing poly-D-lactide, poly-L-lactide, or poly-D,L-lactide as a monomer, and specific examples thereof include polylactic acid, poly-L-lactic acid, poly-D-lactic acid, poly-DL-lactic acid, and the like.

The polylactic acid polymers may be mixed with a crystalline homopolylactic acid polymers and an amorphous homopolylactic acid polymers for the purpose of enhancing the solubility in a solvent to prepare a film coating liquid. In this case, the ratio of an amorphous homopolylactic acid polymers only needs to be determined to the extent that the desired effects are not impaired. In addition, when it is desired to impart relatively high heat resistance to the biodegradable material layer, the layer preferably contains polylactic acid polymers at least one of which has an optical purity of 95% or more.

The polylactic acid polymers preferably contain poly-L-lactic acid (L-isomer) and/or poly-D-lactic acid (D-isomer) as a main component(s). The main component refers to a lactic-acid-derived component of 70 mol % or more but 100 mol % or less with respect to 100 mol % of all monomer components constituting the polylactic acid polymers, and homopolylactic acid polymers composed substantially of only poly-L-lactic acid and/or poly-D-lactic acid are preferably used.

In addition, the amount of poly-D-lactic acid with respect to 100 mol % of the whole polylactic acid polymers is preferably 4 mol % to 50 mol %, more preferably 6 mol % to 13 mol %. When the amount of poly-D-lactic acid is 4 mol % or more with respect to 100 mol % of the whole polylactic acid polymers, the polymer is easy to form into a coating agent because it has suitable solubility into an organic solvent, and when the amount of poly-D-lactic acid is 50 mol % or less with respect to 100 mol % of the whole polylactic acid polymer, the polymer is preferable because it does not adversely affect metabolism.

The polylactic acid polymers may be a copolymerized polylactic acid polymers in which not only L-lactic acid and D-lactic acid but also other monomer components having an ester forming ability are copolymerized. Examples of copolymerizable monomer components include: hydroxycarboxylic acids such as glycolic acid, 3-hydroxybutyric acid, 4-hydroxybutyric acid, 4-hydroxyvaleric acid, and 6-hydroxycaproic acid; compounds containing a plurality of hydroxyl groups in the molecule such as ethylene glycol, propylene glycol, butanediol, neopentyl glycol, polyethylene glycol, glycerin, and pentaerythritol, or derivatives thereof; compounds containing a plurality of carboxylic groups in the molecule such as succinic acid, adipic acid, sebacic acid, fumaric acid, terephthalic acid, isophthalic acid, 2,6-naphthalenedicarboxylic acid, 5-sodium-sulfoisophthalic acid, and 5-tetrabutylphosphonium-sulfoisophthalic acid, or derivatives thereof. In this regard, it is preferable to select a component having biodegradability from among the above-mentioned copolymerizable components in accordance with the application. These copolymerizable components preferably have a 40 mol % or less content with respect to 100 mol % of all monomer components constituting a polylactic acid polymer.

Examples of polylactic acid polymers production methods include a method of direct polymerization from lactic acid, a method of ring-opening polymerization via lactide and the like, and will be described in detail below.

The polylactic acid polymers preferably has a carboxyl group terminal concentration of 30 eq/$10^3$ kg or less, more preferably 20 eq/$10^3$ kg or less, still more preferably 10 eq/$10^3$ kg or less, in terms of inhibiting hydrolysis from reducing the strength and of imparting good durability (long-term storage stability). It is preferable to use a polylactic acid polymer having a carboxyl group terminal concentration of 30 eq/$10^3$ kg or less, in that the polymer can afford practically good durability because the concentration of carboxy group terminals, which also result in autocatalysis for hydrolysis, is sufficiently low. The lower limit of the carboxyl group terminal concentration of the polylactic acid polymer is not limited to a particular value, and a value sufficiently near 0 eq is no problem.

Examples of methods of controlling the carboxyl group terminal concentration of a polylactic acid polymer to 30 eq/$10^3$ kg or less include: a control method in which a catalyst and a heat history are used when a polylactic acid polymer is synthesized; a method in which a heat history is reduced by lowering the processing temperature during the layer-formation or shortening the heating time; a method in which a reaction type compound is used to block the carboxyl group terminals of a polylactic acid polymer; and the like.

In a method in which a reaction type compound is used to block the carboxyl group terminals of a polylactic acid polymer, at least part of the carboxyl group terminals of the polylactic acid polymer are preferably blocked, and more preferably, all thereof are blocked. Examples of reaction type compounds include: condensation reaction type compounds such as aliphatic alcohols and amide compounds; and addition reaction type compounds such as carbodiimide compounds, epoxy compounds, and oxazoline compounds; in which addition reaction type compounds are preferable in that they are less likely to generate surplus by-products during reaction, and among others, carbodiimide compounds are preferable from the viewpoint of reaction efficiency.

As an impact resistance modifier used to enhance the impact resistance, an aliphatic polyester other than a polylactic acid polymer is preferable in view of fact that the aliphatic polyester has suitable dispersibility in a polylactic acid polymer and that a small amount of the aliphatic polyester can achieve a higher effect.

The aliphatic polyester other than a polylactic acid polymer is not limited to a particular one, and specific examples of polyglycolic acid, poly-3-hydroxybutyric acid, poly-4-hydroxybutyric acid, poly-4-hydroxyvaleric acid, poly-3-hydroxyhexanoic acid or polycaprolactone, polyethylene adipate, polyethylene succinate, polybutylene succinate, poly(butylene succinate-co-adipate) and the like.

To enhance the mechanical strength further and maintain biodegradability, a polybutylene succinate polymer, which is an aliphatic polyester other than a polylactic acid polymer, is preferably used. More preferable is polybutylene succinate or poly(butylene succinate-co-adipate), which has a high effect of enhancing the mechanical strength and has good compatibility with a polylactic acid polymer.

The polybutylene succinate polymers preferably has a weight-average molecular weight of 100,000 to 300,000. In this regard, a polybutylene succinate polymer is obtained by polycondensation of 1,4-butanediol and succinic acid.

The polylactic acid polymers can be obtained, using, for example, the following method. As a raw material, L-lactic acid or D-lactic acid which is a lactic acid component, together with a hydroxycarboxylic acid other than the above-mentioned lactic acid component, can be used. In addition, a cyclic ester intermediates of the hydroxycarboxylic acid can be used as a raw material, examples of lactide, glycolide and the like. Furthermore, dicarboxylic acids, glycols and the like can be used.

Polylactic acid polymers can be obtained using a method in which a raw material such as the above-mentioned lactide, glycolide and the like is allowed to directly undergo dehydration condensation or a method in which the above-mentioned cyclic ester intermediate is allowed to undergo ring-opening polymerization. For example, in a production method by direct dehydration condensation, a high molecular weight polymer is obtained through polymerization using a method in which lactic acids or lactic acids and hydroxycarboxylic acids are allowed to undergo azeotropic dehydration condensation in the presence of preferably an organic solvent, particularly a phenyl ethers solvent; water is preferably removed from the solvent distilled by the azeotropy, whereby the solvent is made substantially anhydrous; and the solvent is returned into the reaction system.

It is also known that a high molecular weight polymer is obtained by allowing a cyclic ester intermediate such as lactide to undergo ring-opening polymerization under reduced pressure using a catalyst such as tin octylate. In this process, a polymer having a small amount of lactide can be obtained using a method in which the conditions for removing moisture and low molecular weight compounds are adjusted when the reactant is heated under reflux in an organic solvent; a method in which the catalyst is deactivated after completion of the polymerization reaction to suppress the depolymerization reaction; a method in which the produced polymer is heat-treated; and the like.

Water-Soluble Polymer (a), Water-Soluble Polymer (b), and Water-Soluble Polymer (c)

The water-soluble polymer (a), water-soluble polymer (b), and water-soluble polymer (c) are high polymer substances that can be dissolved in water, warm water, physiological saline, and an aqueous solution such as a glucose solution. Preferable specific examples are polyvinyl alcohol or copolymers, polysaccharides such as dextran, agarose, pullulan, chitosan, mannan, carrageenan, alginic acid, starches (oxidized starches, etherified starches, dextrin, and the like), amylose, amylopectin, pectin, lentinan, hyaluronic acid, hylan, and cellulose derivatives (methyl cellulose, ethyl cellulose, carboxymethyl cellulose, carboxyethyl cellulose, hydroxyethyl cellulose, hydroxypropyl cellulose, and the like); polypeptides such as gelatin, collagen, elastin, albumin, hemoglobin, transferrin, globulin, fibrin, fibrinogen, and keratin sulfuric acid; polyester copolymers containing polar groups such as polyvinylpyrrolidone and sulfoisophthalic acid; vinylpolymers such as polyhydroxyethyl methacrylate or copolymers; acrylic polymers; urethane polymers; ether polymers; and the like. In addition, polymers in which these various polymers are modified with a functional group such as carboxyl group, amino group, methylol group and the like, can preferably be used. Among others, polyvinyl alcohol and pullulan are preferable from the viewpoint of production cost, availability, and health.

The above-mentioned polyvinyl alcohol is a saponified product of polyvinyl acetate, and the degree of saponification is preferably 80 mol % to 99.9 mol %, more preferably 85 mol % to 98 mol %. When the degree of saponification of polyvinyl alcohol is more than 99.9 mol %, the obtained fabric structure, first film, and second film may have lower solubility in water or an aqueous solution, but polyvinyl alcohol can be used in the water-soluble polymer (a), water-soluble polymer (b), and water-soluble polymer (d) in accordance with the purpose such as adjustment of the dissolution time. In this regard, the polyvinyl alcohol encompasses polyvinyl alcohol copolymers. The polyvinyl alcohol copolymers have a vinyl alcohol unit of preferably 80 mol % to 98 mol %, more preferably 85 mol % to 98 mol %.

The above-mentioned degree of saponification refers to the ratio (mol %) of the number of moles of a vinyl alcohol unit to the total number of moles of the vinyl alcohol unit and a structural unit (typically a vinyl ester unit) that can be converted to a vinyl alcohol unit by saponification both of which units are in a polyvinyl alcohol or a copolymer thereof. In this regard, degree of saponification can be measured in accordance with JIS K6726:1994.

Pullulan is usually advantageous from the viewpoint of availability and price, and pullulan produced by culturing a yeast such as belonging to the genus *Aureobasidium* in a culture medium containing a starch degradation product is advantageously used. For example, PULLULAN (made by Hayashibara Co., Ltd.; Pullulan listed in The Japanese Pharmacopoeia) can suitably be used. Without limitation, however, other Pullulan products can be used, without departing from the spirit and scope of this disclosure. Alternatively, if necessary, maltotriose derivatized by a modifying action such as esterification at any degree of substitution may be used as a repeat unit. The Pullulan preferably has a weight-average molecular weight of usually 5,000 or more, preferably 10,000 to 1,000,000, more preferably 50,000 to 500,000. The weight-average molecular weight and molecular weight distribution of Pullulan can be selected so that the Pullulan can be regulated to a desired disintegration rate. Although depending on the other components to be blended, a weight-average molecular weight of less than 5,000 may make it difficult to form a film in sheet form, and that of more than 1,000,000 may cause the rate of dissolution in an aqueous solvent to be too small.

A water-soluble polymer constituting the water-soluble polymer (a), water-soluble polymer (b), and water-soluble polymer (c) has an average degree of polymerization of preferably 100 to 5,000, more preferably 200 to 2,500, still more preferably 400 to 1,800. The average degree of polymerization refers to a number-average degree of polymerization. An average degree of polymerization in these ranges is preferable in that it is easy to form a uniform coating film, the mechanical strength of the coating film is high, and further the film has excellent redissolvability in an aqueous solution. As used herein, an average degree of polymerization of polyvinyl alcohol refers to an average degree of polymerization measured in accordance with the description of JIS K6726:1994.

A mixture of two or more water-soluble polymers having different average degrees of polymerization may be used. This is preferable not only in that the coating film has high mechanical strength and redissolvability in an aqueous solution, but also in that the coating film is obtained such that the adhesiveness to a base film and the adhesiveness to a polylactic acid polymer are good.

It is preferable to use a mixture which includes each of a water-soluble polymer having a low degree of polymerization, i.e., an average degree of polymerization of 100 to 800, and a water-soluble polymer having a high degree of polymerization, i.e., an average degree of polymerization of 1,000 to 2,500, and which may further include one or more thereof. A water-soluble polymer having a low degree of polymerization preferably has an average degree of polymerization of 300 to 700. A water-soluble polymer having a high degree of polymerization preferably has an average degree of polymerization of 1,300 to 1,700.

Various additives may be added, the added amount of which is 30 mass % or less with respect to 100 mass % of the whole water-soluble polymer (a), water-soluble polymer (b), or water-soluble polymer (d) to the extent that the desired effects are not impaired. The lower limit is not limited to a particular value, and it is no problem if the added amount of the various additives is 0 mass % with respect to 100 mass % of the whole polymer. Examples of usable additives include antioxidants, weathering agents, heat stabilizers, lubricants, nucleating agents, ultraviolet absorbers, coloring agents and the like. In addition, inorganic or organic particles may be added at 20 mass % or less with respect to 100 mass % of the whole polymer to the extent that the desired effects are not impaired. The lower limit is not limited to a particular value, and it is no problem if the added amount of the various additives is 0 mass % with respect to 100 mass % of the whole polymer. Examples of usable additives include: calcium carbonate, titanium oxide, silicon oxide, calcium fluoride, lithium fluoride, alumina, barium sulfate, zirconia, calcium phosphate, cross-linked polystyrenes particle, and metal nanoparticles; and the like.

First Film Containing Water-Soluble Polymer (a) and Second Film Containing Water-Soluble Polymer (c)

The fabric structure containing the water-soluble polymer (b), the first film containing the water-soluble polymer (a), and the second film containing the water-soluble polymer (c) can be laminated with a small amount of water because they each contain a water-soluble polymer, and thus the fabric structure has excellent adhesiveness with the first film and the second film, the laminate is more stable to external stress, and the handling properties of the laminate are enhanced.

The thickness of the first film containing the water-soluble polymer (a) is preferably 1 to 20 μm, more preferably 2 to 10 μm, from the viewpoint of the adhesive strength to the fabric structure containing the water-soluble polymer (b), the handling properties of the laminate, and the shape conformability to an adherend. When it is thinner than 1 μm, the film may be difficult to handle as a single film and make the attaching step difficult. When it is thicker than 20 μm, the adhesiveness to an adherend may be reduced because wrinkles occur to the film attached to the adherend and the first film takes a longer time to redissolve in water or an aqueous solution, making it difficult for the film to be separated from the biodegradable material layer.

The thickness of the second film containing the water-soluble polymer (a) is preferably 1 μm to 20 μm, more preferably 5 μm to 20 μm, from the viewpoint of the adhesive strength to the fabric structure containing the water-soluble polymer (b), the handling properties of the laminate, and the shape conformability to adherends. When it is thinner than 1 μm, the film may be difficult to handle as a single film and make the attaching step difficult, and in addition, the time of redissolution in water or an aqueous solution is too short, and the insertion into a trocar with the inner wall wet may be made difficult. When it is more than 20 μm, the adhesiveness to an adherend may be reduced, because wrinkles may occur in the laminate attached to the adherend and it takes a longer time to redissolve in water or an aqueous solution, making it difficult for the film to be separated from the biodegradable material layer.

Fabric Structures Containing Water-Soluble Polymer (b)

The fabric structures may be constituted of textiles such as belt form, string form, thread form or the like, not to mention fabric forms. As textile, woven fabrics, knitted fabrics, and nonwoven fabrics are preferable, and they may be composite materials. Nonwoven fabrics are desirable from the viewpoint of productivity. In addition, the form of the fibers used for the fabric structure is not limited to a particular one. In addition, the fibers may be composed of one kind of polymer, and may be composed of two or more kinds of polymers.

When the fabric structure is composed of nonwoven fabrics, its production method is not limited to a particular one, and the fabric structure can be obtained using a method in which fleece is formed using a dry method, wet method, meltblowing method, spun bonding method, and the like and then interfiber bonds can be formed using a chemical bonding method, thermal bonding method, needlepunching method, water flow interlacing method and the like.

The above fabric structure preferably has a thickness of 10 μm to 10 mm. Allowing the fabric structure to have a thickness of 10 μm or more enables the fabric structure to have excellent form stability and dimensional stability and enables the suppression of occurrence of processing non-uniformity and breakage due to elongation caused when the fabric structure is laminated to the biodegradable material layer. In addition, allowing the fabric structure to have a thickness of 10 mm or less enables the cushioning properties of the fabric structure to be suitably suppressed, enables a pressing pressure to be suitably maintained on the surface of the fabric structure when the fabric structure is laminated to the biodegradable material layer, and enables efficient laminating processing. In addition, the lower limit of the thickness of the fabric structure is more preferably 50 μm or more, still more preferably 100 μm or more. In addition, the upper limit of the thickness of the fabric structure is more preferably 3 mm or less, still more preferably 1 mm or less.

The above fabric structure contains the water-soluble polymer (b). As mentioned below, this is because containing a water-soluble polymer enables the fabric structure to be dissolved easily with water, an aqueous solution and the like after the laminate is attached to an adherend. The water-soluble polymer (b) is mentioned above.

The average fiber diameter of the fibers in the above fabric structure is preferably 0.001 μm to 100 μm from the viewpoint of solubility in water and fabric strength. The average fiber diameter of the fibers in the fabric structure is preferably 0.1 μm or more, more preferably 1 μm or more. The fabric structure having an average fiber diameter of 0.001 μm or more enables stable yarn-making in spinning. The average fiber diameter of the fabric structure is preferably 100 μm or less, more preferably 50 μm or less. The fabric structure having an average fiber diameter of 100 μm or less enables sufficient flexibility and shape memory ability to be imparted thereto.

The above fabric structure preferably has a mass per unit area of 1 $g/m^2$ to 1,000 $g/m^2$. The above fabric structure has a mass per unit area of more preferably 10 $g/m^2$ or more, still more preferably 15 $g/m^2$ or more. Allowing the above fabric structure to have a mass per unit area of 1 $g/m^2$ or more enables the fabric structure to have better form stability and dimensional stability and enables the suppression of occurrence of processing nonuniformity and breakage due to elongation caused when the fabric structure is laminated to the biodegradable material layer. The above fabric structure has a mass per unit area of more preferably 400 $g/m^2$ or less, still more preferably 150 $g/m^2$ or less. Allowing the above fabric structure to have a mass per unit area of 1,000 $g/m^2$ or less enables the fabric structure to be handled easily when it is made into roll shape, enables the cushioning properties of the fabric structure to be suitably suppressed, enables a pressing pressure to be suitably maintained on the surface of the fabric structure when the fabric structure is laminated to the biodegradable material layer, and enables efficient laminating processing.

The fabric structure may be subjected to treatment such as pressing. Pressing treatment may be carried out between any steps from after the step in which the fabric structure is obtained to after the step in which it is laminated to the first film or the biodegradable material layer. Thermal pressing is preferably carried out to enhance the setting properties when the fabric structure is pressed.

Base Material

A base material in the below-mentioned section of a method of producing the laminate will be described. A base material is used to form the biodegradable material layer, the first film, and the second film.

A base material is preferably a film composed of polymer substances. Examples of film materials used for the base material (hereinafter referred to as base films) include: polyolefins such as polyethylene and polypropylene; polyesters such as polyethylene terephthalate, polybutylene terephthalate, and polyethylene-2,6-naphthalate; polyamides such as nylon 6 and nylon 12; polyvinyl chloride, ethylene vinyl acetate copolymers or saponified products thereof, polystyrene, polycarbonate, polysulfone, polyphenylene oxide, polyphenylene sulfide, aromatic polyamide, polyimide, polyamideimide, cellulose, cellulose acetate, polyvinylidene chloride, polyacrylonitrile, polyvinyl alcohol, these copolymers thereof; and the like. As materials for the base films, polyesters such as polyethylene terephthalate or polyolefins such as polyethylene and polypropylene are preferable, from the viewpoint of the adhesiveness to the first film and the second film and ensuring a uniform film thickness when the materials are layered. Polyesters such as polyethylene terephthalate are particularly preferable because their surface has high wet tensile.

Before the first film and the second film are formed as coating film layers, the base films are more preferably subjected to surface treatment such as corona discharge treatment, flame treatment, plasma treatment, or ultraviolet irradiation treatment.

The base film may be any of an unstretched film, a uniaxially-oriented film, and a biaxially-oriented film, and is preferably a biaxially-oriented film from the viewpoint of dimensional stability and mechanical properties.

In addition, the base film may contain various additives. Examples include antioxidants, weathering agents, heat stabilizers, lubricants, nucleating agents, ultraviolet absorbers, coloring agents and the like. The base film may contain inorganic or organic particles to the extent that the surface smoothness is not significantly impaired. Examples thereof include: particles of talc, kaolinite, calcium carbonate, titanium oxide, silicon oxide, calcium fluoride, lithium fluoride, alumina, barium sulfate, zirconia, mica, calcium phosphate, and cross-linked polystyrene; and the like.

The average particle size of the inorganic or organic particles added to the base film is preferably 0.001 μm to 10 μm, more preferably 0.003 μm to 5 μm. The average particle size refers to a particle size determined by number averaging with photographs taken using a transmission electron microscope and the like at a magnification ratio of 10,000× to 100,000×.

Furthermore, the base films are preferably transparent. The base film has a total light transmittance of preferably 40% or more, more preferably 60% or more, and the upper limit sufficiently near 100% is no problem. The haze of the base film is preferably 20% or less, more preferably 15% or less. A haze of 20% or less is preferable because the biodegradable material layer, the first film, and the second film which are made on the base film are easier to test and check using an optical tester. The lower limit of the haze is not limited to a particular value, and a value sufficiently near 0% is no problem.

Although the thickness of the base films is not limited to a particular value, it is preferably 2 μm to 1,000 μm, and, from the viewpoint of economical efficiency, it is more preferably 10 μm to 500 μm.

Production Method

Next, typical methods of producing the laminate will be described.

Method of Producing Laminate

The method of producing the laminate is not limited to a particular one and, for example, the following method can be used.

(1) forming a layered film in which a biodegradable material layer containing an aliphatic polyester and a first film containing a water-soluble polymer (a) are layered, and a single-film second film containing a water-soluble polymer (c), on two base films respectively;

(2) peeling the formed layered film in which the biodegradable material layer and the first film are layered, and the single film second film, from the base films respectively;

(3) laminating a fabric structure containing a water-soluble polymer (b) to the first film side of the formed and peeled layered film in which the biodegradable material layer and the first film are layered; and then, the second film is laminated to the fabric structure, whereby they are layered and fixed. When they are layered, water or an aqueous solution is provided between the formed and peeled film and the fabric structure by, for example, spraying.

Method of Making Fabric Structure

The production method is not limited to a particular one, and dry spinning in which dope obtained by dissolution in a solvent is extruded through a nozzle into heated air so that the solvent is evaporated and removed is desirable in that the method is widely applicable in accordance with the kind of the water-soluble polymer (b).

Method of Forming Layered Film in which Biodegradable Material Layer Containing Aliphatic Polyester and First Film Containing Water-Soluble Polymer (a) are Layered, and Single-Film Second Film Containing Water-Soluble Polymer (c)

1. Method of Forming Film

Examples of coating methods include, but are not particularly limited to, gravure coating, direct lip coating, slot coating, comma coating, inkjet, silk-screen printing and the like. Examples of base materials include, but are not particularly limited to, glass plates, metal plates, plastic films and the like, and plastic films are desirably used as base films from the viewpoint of economical efficiency, and, plastic films having surface smoothness are particularly desirable.

When a biaxially-oriented film of a polyester such as polyethylene terephthalate or a polyolefin such as polypropylene is used as a base film, either an off-line coating method in which coating is carried out after the film-forming step for the biaxially-oriented film or an in-line coating method in which coating is carried out in the film-forming step for the biaxially-oriented film may be used.

When in-line coating is used, coating is preferably carried out before the film is heat-fixed. Heat-fixation means that an oriented film is crystallized by heat-treatment with the film retained at a temperature higher than the orientation temperature, but lower than the melting point of the film. Accordingly, coating is preferably carried out onto an unstretched film, a film that has just been uniaxially-oriented in the longitudinal direction or cross direction, or a biaxially-oriented film. More preferably, coating is carried out onto a film that has just been uniaxially-oriented, and still more preferably, the film is further oriented biaxially or multiaxially and heat-fixed. Examples of usable methods of drying coating films include heat roll contact, heat medium contact (air, oil and the like), infrared heating, microwave heating and the like.

As a method of forming a coating film on a base film in off-line coating, a method in which a solution with coating film components dispersed in one of various solvents is gravure-coated, reverse-coated, spray-coated, kiss-coated, comma-coated, die-coated, knife-coated, air-knife-coated, or metalling-bar-coated is suitable, in that high speed thin film coating can be carried out thereby. More preferably, the base film is subjected to adhesion promoting treatment before coating such as corona discharge treatment in an atmosphere such as air, nitrogen gas, or a gas mixture of nitrogen and carbon dioxide gas, plasma treatment under reduced pressure, flame treatment, or ultraviolet ray treatment. Further, the base film may be subjected to anchoring treatment using an anchor treatment agent such as a urethane polymer, an epoxy polymer, or polyethyleneimine.

The coating films of the first film containing the water-soluble polymer (a) and the second film containing the water-soluble polymer (c) are dried preferably in the range of 60° C. to 180° C. in off-line coating and 80° C. to 250° C. in in-line coating. The drying time is preferably 1 second to 60 seconds, more preferably 3 seconds to 30 seconds.

The biodegradable material layer containing an aliphatic polyester is preferably dried at 60° C. to 110° C. in off-line coating and 80° C. to 180° C. in in-line coating. The drying time is preferably 1 second to 60 seconds, more preferably 3 seconds to 30 seconds.

2. Peeling from Base Films

Next, the layered film in which the biodegradable material layer containing an aliphatic polyester and the first film containing the water-soluble polymer (a) are layered and the single-film second film containing the water-soluble polymer (c) are mechanically peeled from the base films.

3. Fixation of Single Film or Layered Film on Support

Further, the obtained single film or layered film is placed such that its joining face to the fabric structure does not come in contact with a support. Examples of supports include, but are not particularly limited to, glass plates, metal plates, plastic films and the like, and plastic films are preferably used as supports from the viewpoint of economical efficiency, and plastic films having surface releasability are particularly preferable.

4. Making Laminate

A method of laminating the single film and the layered film to the fabric structure is not limited to a particular one, and the laminate in which the biodegradable material layer and the water-soluble material layer are layered is formed by: spraying water or an aqueous solution onto the fabric structure to thereby dissolve its sides; allowing the surface of the first film of the layered film to be contacted with and deposited on one side of the fabric structure; and allowing the second film to be contacted with and deposited on the other side of the fabric structure.

Examples of aqueous solutions include, but are not particularly limited to, pure water, alcohol aqueous solutions, mineral dispersions, pharmaceutical-dispersed aqueous solutions, and the like and pure water is desirable from the viewpoint of economy.

Method of Spraying Water or Aqueous Solution

A method of spraying water or an aqueous solution is not limited to a particular one and may be any of those in which liquid can be widely and uniformly scattered in fine shape using a spraying device such as a spray or a shower and, for example, an accumulator spray method, a nozzle spray method (two-fluid nozzle, three-fluid nozzle, or four-fluid nozzle), an inkjet method and the like can be used.

Laminating Method

A method of laminating the biodegradable material layer, the first film, and the second film to the fabric structure for the laminate may be any method, and the below-mentioned two laminating methods: Laminating Methods A and B are preferable.

Laminating Method A: a method in which, while a layered film in which a biodegradable material layer and a first film are layered and a single film second film are fixed on separate flat plates, a fabric structure is laminated to each of the films.

Laminating Method B: a method in which a layered film in which a biodegradable material layer and a first film are layered, a fabric structure, and a single film second film are layered in this order, and the resulting multilayer is put between two rolls and thereby laminated.

Coating Agent Containing Water-Soluble Polymer (a), Water-Soluble Polymer (b), or Water-Soluble Polymer (c)

Coating agents containing the water-soluble polymer (a), the water-soluble polymer (b), or the water-soluble polymer (c) respectively can be used when a fabric structure, a first film, and a second film containing the respective water-soluble resins are laminated.

A coating agent containing the water-soluble polymer (a), the water-soluble polymer (b), or the water-soluble polymer (c) is preferably a solution in which the components thereof are uniformly dissolved. As the solvent, water or a solution mixture of water and lower alcohol is preferably used. A solution mixture of water and lower alcohol is more preferably used.

The solid content concentration of a coating agent containing the water-soluble polymer (a), the water-soluble polymer (b), or the water-soluble polymer (c) is preferably 1.0 mass % or more and preferably 15 mass % or less from the viewpoint of productivity, for example, the viscosity, drying efficiency, and coating properties of the coating agent. Using a coating agent having too high a concentration of more than 15 mass % results in too high solution viscosity and may make it difficult to control the thickness of the first film and that of the second film. In using a coating agent having a low concentration of less than 1.0 mass %, used is a method in which a highly volatile low boiling point solvent having affinity with water is added to a solvent for the coating agent; a method in which the coating film is dried at a temperature equal to or higher than the boiling point of water; or the like.

In addition, to have coatability imparted thereto, the solvent mixture may contain another water-soluble organic compound as a third component to the extent that the coating agent containing the water-soluble polymer (a), the water-soluble polymer (b), or the water-soluble polymer (c) can maintain stability. Examples of water-soluble organic compounds include: alcohols such as methanol, ethanol, n-propanol, and isopropanol; glycols such as ethylene glycol and propylene glycol; glycol derivatives such as methylcellosolve, ethylcellosolve, and n-butylcellosolve; polyalcohols such as glycerin and waxes; ethers such as dioxane; esters such as ethyl acetate; and ketones such as methyl ethyl ketone. In addition, the pH of the dispersion is preferably 2 to 11 from the viewpoint of the stability of the solution.

Coating Agent Containing Aliphatic Polyester

As the coating agent containing an aliphatic polyester, a solution in which the components thereof are uniformly dissolved is preferable. Examples of solvents to be preferably used include, but are not particularly limited to, at least one single solvent or a solution mixture of two or more solvents selected from the group consisting of butyl alcohol, chloroform, cyclohexane, acetonitrile, dichloromethane, dichloroethane, ethyl acetate, ethyl ether, dipropyl ether, and toluene. Ethyl acetate is particularly preferable from the viewpoint of productivity and handling properties.

The solid content concentration of a coating agent containing an aliphatic polyester is, without particular limitation, preferably 1.0 mass % or more and preferably 10 mass % or less in terms of productivity, for example, the viscosity, drying efficiency, and coating properties of the coating agent.

In addition, to have coatability imparted thereto, the solution may contain another organic compound as a third component to the extent that the coating agent containing an aliphatic polyester can maintain stability.

Method of Preparing Coating Agent

A method of preparing a coating agent containing the water-soluble polymer (a), the water-soluble polymer (b), or the water-soluble polymer (c) and a coating agent containing an aliphatic polyester is not limited to a particular one, but when various additives such as cross-linked agents and particles are added to the extent that the desired effects are not impaired, the method is preferably such that the polymers and the additives are uniformly dispersed in a coating agent. If necessary, a method in which the solubility of the polymers is increased by increasing the temperature of the solvent using a heater and the like or a method in which mechanically enforced dispersion treatment is carried out using a device that applies shearing force and shearing stress such as a homomixer, a jet agitator, a ball mill, a bead mill, a kneader, a sand mill, or a three-roll mill and the like may be used.

Method of Using Laminate

In an abdominal cavity surgery, a method in which an endoscope is used through a small hole made in the abdominal cavity is less burdensome for the human body and thus more preferable than a celiotomy. In this case, the laminate will pass through a thin tubular container such as a trocar and be attached to a site of interest. In this case, the laminate is suitably used particularly in surgeries in which an endoscope is used, because the laminate has a good passing characteristic into a trocar and good spreadability achieved after the laminate passes out of the trocar, (good spreadability means that, after the laminate is once pressed into a trocar and the like and then passes out of the trocar and the like, the laminate can easily be spread into the nearly original form using forceps and the like).

The laminate has, for example, such a structure as shown in FIG. 1. In other words, it is a laminate 5 including a 10 nm to 500 nm thick biodegradable material layer 1 containing an aliphatic polyester and a water-soluble material layer which is layered on one side of the biodegradable material layer and in which a 1 μm to 20 μm thick first film 2 containing a water-soluble polymer (a), a 10 μm to 10 mm thick fabric structure 3 containing a water-soluble polymer (b), and a 1 μm to 20 μm thick second film 4 containing a water-soluble polymer (c) are layered in this order from the biodegradable material layer.

Figure 2:
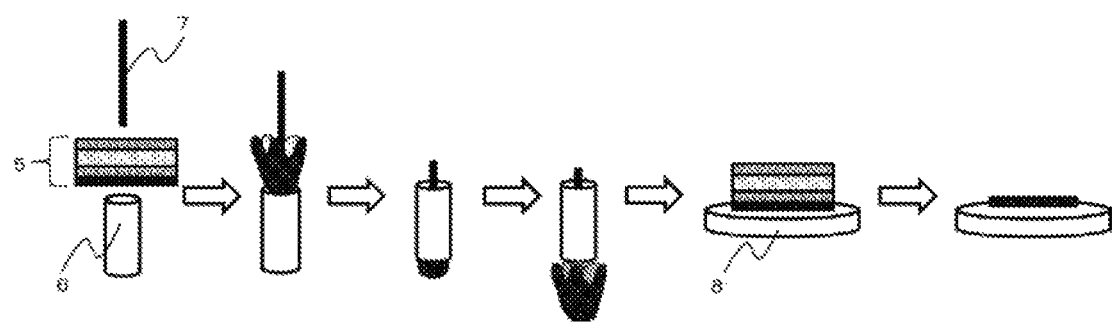
FIG. 2 is a schematic view depicting an example of a method of using the laminate.

Examples of methods of using the laminate include a using method shown in FIG. 2. In other words, the laminate 5 is pushed into a tubular container 6 through one of the openings of the container 6 using a pushing jig 7, the laminate 5 is sent out through the other of the openings, and the laminate 5 is attached to the surface of an adherend 8. In the method, the laminate 5 is then sprayed with water or an aqueous solution, the water-soluble material layer (the first film 2, the fabric structure 3, and the second film 4) is thereby dissolved and removed, and the biodegradable material layer 1 (shown in FIG. 1) is allowed to remain on the surface of the adherend 8.

EXAMPLES

Below, Examples and Comparative Examples (Examples 1 to 12 and Comparative Examples 1 to 9) for the laminate will be described. First, the characteristics evaluation methods are as follows:

(1) Mass Per Unit Area of Fabric Structure

The mass per unit area was measured using the method described in JIS L 1096 8.3.2(1999). Two 200 mm square test pieces were taken, their masses (g) per unit area in normal state were weighed, the masses (g/m$^2$) per m$^2$ were determined using the following formula, and the average thereof was calculated and rounded off to the nearest whole number:

$$Sm=W/A$$

wherein Sm: mass (g/m$^2$) per unit area in normal state
W: mass (g) of test piece in normal state
A: area (m$^2$) of test piece.
In this regard, normal state means a temperature of 20±2° C. and a relative humidity of 65±4% in accordance with JIS L 0105 5.2(2006).
(2) Method of Measuring Thickness of Each of Laminate, Biodegradable Material Layer, First Film, Fabric Structure, and Second Film:

When the laminate was measured as it was, a dial thickness gauge (tradename: PEACOCK H; made by Ozaki Mfg. Co., Ltd.; scale interval: 0.01 mm; measuring force: 1.8 N or less) was used first to measure 10 points each in Examples 1 to 12 and Comparative Examples 1 to 9, and the average value thereof was regarded as the total thickness of the laminate. However, when the total thickness was less than 0.05 mm, a more accurate high dial thickness gauge (SM-1201L made by TECLOCK Corporation; scale interval: 0.001 mm; measuring force: 1.5 N or less) was used.

Next, to measure the thickness of each layer, a cross-section perpendicular to the thickness direction was made using a microtome, and a scanning electron microscope (Model VE-7800 made by Keyence Corporation) was used to observe each layer at a magnification ratio suitably adjusted in the range of 2,500× to 100,000× such that the layer to be observed fitted into 10% to 90% of the viewing angle. The average value of the values measured from different 10 cross-sections in the same Example or Comparative Example was regarded as the thickness of each layer. When the thickness of each layer was 0.1 μm or less and it was difficult to observe using the above-mentioned method, a high-resolution transmission electron microscope (JEM-2100 made by JEOL Ltd.) was used to observe in the same manner but at a magnification ratio 500,000× to 1,000,000×. When it was still difficult to make a judgement, the observed image was stored, the image was suitably expanded (for example, printed into an A3 size), and the thickness was judged. The thickness of the fabric structure was obtained from the total thickness of the laminate minus the thickness of the biodegradable material layer, the first film, and the second film.
(3) Evaluation of Solubility of Water-Soluble Material Layer (First Film, Fabric Structure, and Second Film) of Laminate:

When the laminate was used as it was to measure the solubility of the water-soluble material layer, the biodegradable material layer was removed first. Specifically, 12 g of ethyl acetate was loaded in a dish (TPX petri dish, deep type, made by Sanplatec Co., Ltd.), a 5 cm square sampled laminate (hereinafter referred to as a test piece) was fixed hanging in midair such that the water-soluble material layer was not immersed in ethyl acetate, and the biodegradable material layer containing fatty acid polyester was immersed in ethyl acetate. Then, the dish was sealed and allowed to stand in a state heated at 35° C. for 30 minutes, ethyl acetate was replaced about 3 times, the test piece was taken out and air-dried, and the biodegradable material layer was thus removed.

The solubility of the water-soluble material layer was evaluated using the following method. An adjustment was made such that the height from the surface of a test piece which had been rid of the biodegradable material layer to the end of a burette was 10 mm. A time taken from a start time to a termination time was measured, in which the start time was the time when one drop (about 0.04 ml) of normal temperature water was dropped from the burette to the surface of the second layer of the test piece which had been rid of the biodegradable material layer, and the termination time was the time when the water permeated to the other side and caused dissolution. The dissolution means that the fiber is broken, being not capable of maintaining its fabric shape, and it is checked by visual observation of the fabric shape from many sides.

The evaluation indices are as follows:
Rating A: the time taken up to the termination of dissolution was 15 seconds or more but less than 3 minutes
Rating B: the time taken up to the termination of dissolution was 5 seconds or more but less than 15 seconds, or 3 minutes or more but less than 5 minutes
Rating C: less than 5 seconds or 5 minutes or more.
(4) Evaluation of Piercing Strength:

The evaluation was carried out using a precision universal testing machine (Autograph AG-I, made by Shimadzu Corporation) with a 50 N load cell mounted thereon and using a piercing rod the end of which is in the shape of a hemisphere having a diameter of 5 mm. The Examples 1 to 12 and Comparative Examples 1 to 9 were each fixed on a retort pouch piercing stand (made by Shimadzu Corporation) and secured such that the second film side of the test piece abutted on the piercing rod. The evaluation was carried out at a stroke speed of 200 mm/min in the testing.

Figure 3:
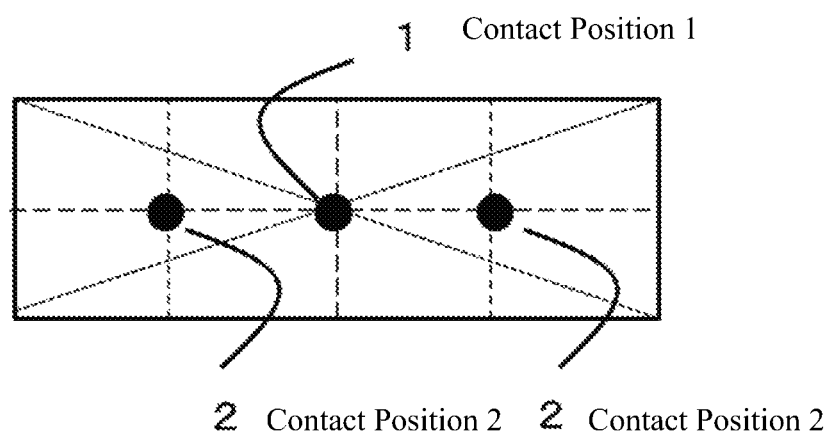
FIG. 3 is a view depicting the contact positions between the advancing rod and the test pieces in the trocar passage evaluation of the laminate.

The evaluation indices are as follows:
Rating A: 0.5 N or more but 30 N or less
Rating B: 0.3 N or more but less than 0.5 N
Rating C: less than 0.3 N or more than 30 N.
(5) Evaluation of Trocar Passing Characteristic:
(a) Trocar Passing Characteristic of Dried Laminate A 7 cm×12 cm test piece was evaluated for flexibility on the following conditions using a trocar expected to be used in laparoscopic surgeries. The trocar and the advancing rod mentioned in (i) below were used. The test piece was placed so that the biodegradable material layer side thereof could come into contact with the inner wall portion of the trocar, then pushed therein, and advanced to thereby evaluate whether the test piece passed through the trocar. When the testing was carried out, the speed at which the test piece was pushed in the trocar was in the range of 200 mm/min to 600 mm/min. The positions at which the advancing rod and the test piece were in contact were as follows (shown in FIG. 3):
Contact position 1: the center of the test piece
Contact position 2: the position 3 cm from the center to the short portion in the longitudinal direction.

In addition, the evaluation indices are as follows:
Rating A: the contact position 1 and the contact position 2 both enabled the test piece to pass through the trocar, and no breakage of the passed test piece was allowed to be visually observed.
Rating B: the contact position 1 and the contact position 2 both enabled the test piece to pass through the trocar, and the contact position 2 allowed no breakage of the passed test piece to be visually observed, but the contact position 1 allowed a slight breakage of the passed test piece to be visually observed.
Rating C: neither the contact position 1 nor the contact position 2 enabled the test piece to pass through the trocar, or, even if it enabled, only a piece broken off the test piece was allowed to pass through.

(i) trocar: ENDOPATH (registered trademark) XCEL bladeless trocar Optiview (registered trademark) (made by Johnson & Johnson K.K.; hole: 12 mm in diameter, tube length: 15.2 mm)

Advancing rod: ENDOPATH (registered trademark) cherry dissector (made by Johnson & Johnson K.K.; end: 10 mm in diameter)

(b) Trocar Passing Characteristic of Wet Laminate

Assuming that the laminate is used during a surgery, the testing was carried out with the inside of the trocar wetted. Specifically, 15 cc of water was kept in a dish (TPX dish of deep type, made by Sanplatec Co., Ltd.), and a piece of gauze (HAIZE (registered trademark) gauze NT-4, made by Ozu Corporation) was placed therein to allow it to absorb sufficient water. The gauze is inserted into the trocar described in (i), and the test piece was passed through the trocar in the same way as in the section of (a) for the dried laminate but with water drops attached to the internal wall. A test piece which successfully passed through the trocar without being broken was rated A, and one which was broken or swollen and failed to pass through the trocar was rated B.

(6) Evaluation of Adhesiveness:

To the center of a polyester film ("LUMIRROR" (registered trademark) #100T60, size: 5 cm×5 cm, made by Toray Industries, Inc.) wetted by a spray of 100 mg of pure water, the biodegradable material layer side of the test piece (size: 3 cm×3 cm) was attached and pressed using a silicone rubber dried for five seconds (hardness: 20°, size: 3 cm×1 cm, made by Kyowa Industrial Co., Ltd.), and thus adhered. Then, the test piece was transferred into a container having a 12 cm×5 cm bottom face, 12 g of pure water was softly poured onto the water-soluble material layer side of the test piece, and the water-soluble material layer of the test piece was dissolved and removed. Next, the test piece together with the polyester film was taken out of the solution, and vertically placed in an environment under a temperature of 25° C. and a relative humidity of 90% in a temperature/humidity chamber (LHU-113, made by Espec Corp.), and allowed to stand for one hour or more, thereby surplus moisture was removed from the test piece.

Subsequently, the test piece together with the polyester film was taken out of the temperature/humidity chamber and checked to see whether the polyester film and the test piece could be slipped off each other using bare hands, and it was rated as Rating A if no slippage occurred and Rating B if any slippage occurred or if the test piece was not successfully checked.

Each of the materials and devices used in Examples 1 to 12 and Comparative Examples 1 to 9 will be described below.

First, the materials used in Examples 1 to 12 and Comparative Examples 1 to 7 will be described.

Base Films Used
Polyester Film-1 (hereinafter referred to as "PET-1":
biaxially-oriented polyester film ("LUMIRROR" (registered trademark), type: T60, thickness: 100 μm, made by Toray Industries, Inc.).
Polylactic Acid Polymers Used
Polylactic Acid Polymer-1 (hereinafter referred to as "PLA-1"):
poly-L-lactic acid-D-lactic acid copolymerization polymer (PURASORB (registered trademark) PDL20, made by Corbion N.V.) having a 50 mol % amount of poly-D-lactic acid with respect to the whole polymer, no melting point (amorphous), and a weight-average molecular weight of 400,000 in terms of PMMA.

Polylactic Acid Polymer-2 (Hereinafter Referred to as "PLA-2"):
poly-L-lactic acid polymer (4060D, made by NatureWorks LLC) having a 12 mol % amount of poly-D-lactic acid with respect to the whole polymer, an amorphous property, and a weight-average molecular weight of 200,000 in terms of PMMA.
Polylactic Acid Polymer-3 (Hereinafter Referred to as "PLA-3"):
poly-L-lactic acid polymer (4032D, made by NatureWorks LLC) having a 1.4 mol % amount of poly-D-lactic acid with respect to the whole polymer and a weight-average molecular weight of 220,000 in terms of PMMA.
Water-Soluble Polymer (a), (b), and (c) Used
Pullulan-1
Pullulan (Pullulan listed in The Japanese Pharmacopoeia) having a weight-average molecular weight of about 300,000, a kinematic viscosity of 100 to 180 $mm^2$/second (viscosity measurement conditions: 30° C. temperature, an aqueous solution having a solid content concentration of 10 mass %).
Polyvinyl Alcohol-1 (Hereinafter Referred to as "PVA-1")
polyvinyl alcohol (JP-10, made by Japan VAM & POVAL Co., Ltd.) having a degree of saponification of 88 mol % and a viscosity of 10 mPa·s (4 mass % aqueous solution, 20° C.).
Polyvinyl Alcohol-2 (Hereinafter Referred to as "PVA-2")
polyvinyl alcohol (JM-17, made by Japan VAM & POVAL Co., Ltd.) having a degree of saponification of 96.5 mol % and a viscosity of 27.5 mPa·s (4 mass % aqueous solution, 20° C.).
Gelatin-1
gelatin powder (gelatin listed in The Japanese Pharmacopoeia, made by Nitta Gelatin Inc.)
Fabric Structure Used Reference Example 1

Yarns having a fiber diameter of 5 μm were obtained by a dry spinning method using Pullulan-1 as the water-soluble polymer (a), cumulated on a collecting conveyor, and made into 300 μm thick nonwoven fabrics composed of Pullulan-1.

Reference Example 2

Yarns having a fiber diameter of 0.1 μm were obtained by a dry spinning method using Pullulan-1 as the water-soluble polymer (a), cumulated on a collecting conveyor, and made into 100 μm thick nonwoven fabrics composed of Pullulan-1.

Reference Example 3

Yarns having a fiber diameter of 100 μm were obtained by a dry spinning method using Pullulan-1 as the water-soluble polymer (a), cumulated on a collecting conveyor, and made into 3,000 μm thick nonwoven fabrics composed of Pullulan-1.

Reference Example 4

Yarns having a fiber diameter of 2 μm were obtained by a dry spinning method using Pullulan-1 as the water-soluble polymer (a), cumulated on a collecting conveyor, and made into 300 μm thick nonwoven fabrics composed of Pullulan-1.

Reference Example 5

Yarns having a fiber diameter of 50 μm were obtained by a dry spinning method using Pullulan-1 as the water-soluble polymer (a), cumulated on a collecting conveyor, and made into 900 μm thick nonwoven fabrics composed of Pullulan-1.

Reference Example 6

Yarns having a fiber diameter of 0.01 μm were obtained by a dry spinning method using Pullulan-1 as the water-soluble polymer (a), cumulated on a collecting conveyor, and made into 450 μm thick nonwoven fabrics composed of Pullulan-1.

Reference Example 7

Yarns having a fiber diameter of 7 μm were obtained by a dry spinning method using PVA-1 as the water-soluble polymer (a), cumulated on a collecting conveyor, and made into 200 μm thick nonwoven fabrics composed of PVA-1.

Reference Example 8

Yarns having a fiber diameter of 5 μm were obtained by a dry spinning method using PVA-1 as the water-soluble polymer (a), cumulated on a collecting conveyor, and made into 300 μm thick nonwoven fabrics composed of PVA-1.

Reference Example 9

Yarns having a fiber diameter of 0.001 μm were obtained by a dry spinning method using PVA-2 as the water-soluble polymer (a), cumulated on a collecting conveyor, and made into 10,000 μm thick nonwoven fabrics composed of PVA-2.

Reference Example 10

Yarns having a fiber diameter of 0.0001 μm were obtained by a dry spinning method using Pullulan-1 as the water-soluble polymer (a), cumulated on a collecting conveyor, and made into 50 μm thick nonwoven fabrics composed of Pullulan-1.

Reference Example 11

Yarns having a fiber diameter of 200 μm were obtained by a dry spinning method using Pullulan-1 as the water-soluble polymer (a), cumulated on a collecting conveyor, and made into 1,000 μm thick nonwoven fabrics composed of Pullulan-1.

Reference Example 12

Yarns having a fiber diameter of 100 μm were obtained using Gelatin-1 as the water-soluble polymer (a) by a method of melt-extrusion into an alcohol solution, cumulated on a collecting conveyor, and made into 2,000 μm thick nonwoven fabrics composed of Gelatin-1.

Reference Example 13

Yarns having a fiber diameter of 50 μm were obtained by a dry spinning method using PVA-2 as the water-soluble polymer (a), cumulated on a collecting conveyor, and made into 15,000 μm thick nonwoven fabrics composed of PVA-2.

Example 1

Pullulan-1 was used as the water-soluble polymer (a) and the water-soluble polymer (c) to thereby make the first film containing the water-soluble polymer (a) and the second film containing the water-soluble polymer (c). Specifically, Pullulan-1 was dissolved in water using a heating type homogenizer, and made into an emulsion containing the water-soluble polymer. One side each of two base films was coated with Pullulan-1 using an applicator method so that each film could have a film thickness of 5 μm when dried later, and then dried in a hot-air dryer at 90° C. for 20 seconds to form the first film containing the water-soluble polymer (a) and the second film containing the water-soluble polymer (c).

In addition, the biodegradable material layer containing an aliphatic polyester was made using PLA-1 as a fatty acid polyester. Specifically, using a metalling bar, the first film containing the water-soluble polymer (a) formed on a base film was coated with a solution of PLA-1 dissolved in ethyl acetate so that the film could have a thickness of 150 nm when dried later, and then dried in a hot-air dryer at 80° C. for 20 seconds to make a layered film including the biodegradable material layer containing an aliphatic polyester and the first film containing the water-soluble polymer (a).

The layered film in which the biodegradable material layer containing an aliphatic polyester and the first film containing the water-soluble polymer (a) were layered, and the second layer containing the water-soluble polymer (c) were peeled from the base film. Then, using a spray, the first film side of the layered film was coated with pure water at 5 g/m², and the 300 μm thick nonwoven fabric composed of Pullulan-1 in Reference Example 1 was laminated to the first film. Then, the second film was laminated to the other side of the nonwoven fabric, whereby a laminate having the biodegradable material layer and the water-soluble material layer was made.

Example 2

A laminate having the biodegradable material layer and the water-soluble material layer was made in the same manner as in Example 1 except that the thickness of the biodegradable material layer was changed to 200 nm, the thickness of the first film was changed to 10 μm, and the 100 μm thick nonwoven fabric composed of Pullulan-1 (Reference Example 2) was used as the fabric structure.

Example 3

A laminate having the biodegradable material layer and the water-soluble material layer was made in the same manner as in Example 1 except that the thickness of the biodegradable material layer was changed to 300 nm, the 3,000 μm thick nonwoven fabric composed of Pullulan-1 (Reference Example 3) was used as the fabric structure, and the thickness of the second film was changed to 1 μm.

Example 4

A laminate having the biodegradable material layer and the water-soluble polymer material layer was made in the same manner as in Example 1 except that the thickness of the biodegradable material layer was changed to 500 nm, the thickness of the first film was changed to 12 μm, the 300 μm thick nonwoven fabric composed of Pullulan-1 (Reference Example 4) was used as the fabric structure, and the thickness of the second film was changed to 6 μm.

Example 5

A laminate having the biodegradable material layer and the water-soluble material layer was made in the same manner as in Example 1 except that the thickness of the first film was changed to 1 μm, and the thickness of the second film was changed to 20 μm.

Example 6

A laminate having the biodegradable material layer and the water-soluble material layer was made in the same manner as in Example 1 except that the thickness of the biodegradable material layer was changed to 100 nm, the thickness of the first film was changed to 8 μm, and the thickness of the second film was changed to 2 μm.

Example 7

A laminate having the biodegradable material layer and the water-soluble material layer was made in the same manner as in Example 1 except that the thickness of the biodegradable material layer was changed to 250 nm, the thickness of the first film was changed to 3 μm, the 900 μm thick nonwoven fabric composed of Pullulan-1 (Reference Example 5) was used as the fabric structure, and the thickness of the second film was changed to 3 μm.

Example 8

A laminate having the biodegradable material layer and the water-soluble material layer was made in the same manner as in Example 1 except that the thickness of the biodegradable material layer was changed to 20 nm, the thickness of the first film was changed to 8 μm, the 450 μm thick nonwoven fabric composed of Pullulan-1 (Reference Example 6) was used as the fabric structure, and the thickness of the second film was changed to 8 μm.

Example 9

A laminate having the biodegradable material layer and the water-soluble material layer was made in the same manner as in Example 1 except that the thickness of the first film was changed to 20 μm, the 200 μm thick nonwoven fabric composed of PVA-1 (Reference Example 7) was used as the fabric structure, and the thickness of the second film was changed to 3 μm.

Example 10

A laminate having the biodegradable material layer and the water-soluble material layer was made in the same manner as in Example 1 except that the thickness of the biodegradable material layer was changed to 80 nm, the thickness of the first film was changed to 6 μm, and the second film was changed to a 12 μm thick film composed of PVA-1.

Example 11

A laminate having the biodegradable material layer and the water-soluble material layer was made in the same manner as in Example 1 except that the first film was changed to a 5 μm thick film composed of PVA-1, and the 300 μm thick nonwoven fabric composed of PVA-1 (Reference Example 8) was used as the fabric structure.

Example 12

A laminate having the biodegradable material layer and the water-soluble material layer was made in the same manner as in Example 1 except that the thickness of the biodegradable material layer was changed to 10 nm, the aliphatic polyester was changed to PLA-2, the first layer was changed to a 5 μm thick film composed of PVA-2, the 10,000 μm thick nonwoven fabric composed of PVA-2 (Reference Example 9) was used as the fabric structure, and the second film was changed to a 3 μm thick film composed of PVA-2.

Comparative Example 1

A laminate having the biodegradable material layer and the water-soluble material layer was made in the same manner as in Example 1 except that the thickness of the second film was changed to 25 μm.

Comparative Example 2

A laminate having only the water-soluble material layer was made in the same manner as in Example 1 except that the first film, the fabric structure, and the second film were laminated together with the biodegradable material layer not layered therewith.

Comparative Example 3

An attempt was made to make a laminate in the same manner as in Example 1 except that the 50 μm thick nonwoven fabric composed of Pullulan-1 (Reference Example 10) was used as the fabric structure, but the fabric structure melted when the layered film containing the first film and the biodegradable material layer was laminated to the fabric structure, resulting in failure to make the laminate.

Comparative Example 4

A laminate having the biodegradable material layer and the water-soluble material layer was made in the same manner as in Example 1 except that the thickness of the biodegradable material layer was changed to 2,000 nm.

Comparative Example 5

The 1,000 μm thick nonwoven fabric composed of Pullulan-1 (Reference Example 11) was used as the fabric structure, and none of the biodegradable material layer, the first film, and the second film was made, but only the fabric structure of Reference Example 11 was used.

Comparative Example 6

A laminate having only the water-soluble material layer was made in the same manner as in Example 1 except that the 2,000 μm thick nonwoven fabric composed of Gelatin-1 (Reference Example 12) was used as the fabric structure, and the biodegradable material layer was not laminated together.

Comparative Example 7

A laminate having a first biodegradable material layer and a second biodegradable material layer was made in the same manner as in Example 1 except that the thickness of the biodegradable material layer was changed to 500 nm, and a 500 μm thick second biodegradable material layer composed of PLA-1 was further layered on the external side of the second film.

Comparative Example 8

The 15,000 μm thick nonwoven fabric composed of PVA-2 (Reference Example 13) was used as the fabric structure, and the first film was removed using water or an aqueous solution before the layered film containing the first film and the biodegradable material layer was laminated to the fabric structure. The subsequent procedure was carried out in the same manner as in Example 1 except that the biodegradable material layer and the fabric structure were directly laminated together with the second film not laminated therewith. Thus, the laminate in which the biodegradable material layer was layered on one side of the fabric structure containing the water-soluble polymer (b) was made.

The characteristics results in Examples 1 to 12 and Comparative Examples 1 to 9 are shown in Tables 1 to 4.

TABLE 1

| Item 1 | Item 2 | Example 1 | Example 2 | Example 3 | Example 4 | Example 5 | Example 6 |
|---|---|---|---|---|---|---|---|
| Biodegradable Polymer Layer | Polymer | PLA-1 | PLA-1 | PLA-1 | PLA-1 | PLA-1 | PLA-1 |
| | Thickness (nm) | 150 | 200 | 300 | 500 | 150 | 100 |
| First Layer | Polymer | Pullulan-1 | Pullulan-1 | Pullulan-1 | Pullulan-1 | Pullulan-1 | Pullulan-1 |
| | Thickness (μm) | 5 | 10 | 5 | 12 | 1 | 8 |
| Fabric Structure | Designation | Reference Example 1 | Reference Example 2 | Reference Example 3 | Reference Example 4 | Reference Example 1 | Reference Example 1 |
| | Polymer | Pullulan-1 | Pullulan-1 | Pullulan-1 | Pullulan-1 | Pullulan-1 | Pullulan-1 |
| | Fabric Diameter (μm) | 5 | 0.1 | 100 | 2 | 5 | 5 |
| | Thickness (μm) | 300 | 100 | 3,000 | 300 | 300 | 300 |
| Second Layer | Polymer | Pullulan-1 | Pullulan-1 | Pullulan-1 | Pullulan-1 | Pullulan-1 | Pullulan-1 |
| | Thickness (μm) | 5 | 5 | 1 | 6 | 20 | 2 |

| Item 1 | Example 7 | Example 8 | Example 9 | Example 10 | Example 11 | Example 12 |
|---|---|---|---|---|---|---|
| Biodegradable Polymer Layer | PLA-1 | PLA-1 | PLA-1 | PLA-1 | PLA-1 | PLA-2 |
| | 250 | 20 | 150 | 80 | 150 | 10 |
| First Layer | Pullulan-1 | Pullulan-1 | Pullulan-1 | Pullulan-1 | PVA-1 | PVA-2 |
| | 3 | 8 | 20 | 6 | 5 | 5 |
| Fabric Structure | Reference Example 5 | Reference Example 6 | Reference Example 7 | Reference Example 1 | Reference Example 8 | Reference Example 9 |
| | Pullulan-1 | Pullulan-1 | PVA-1 | Pullulan-1 | PVA-1 | PVA-2 |
| | 50 | 0.01 | 7 | 5 | 5 | 0.001 |
| | 900 | 450 | 200 | 300 | 300 | 10,000 |
| Second Layer | Pullulan-1 | Pullulan-1 | Pullulan-1 | PVA-1 | Pullulan-1 | PVA-2 |
| | 3 | 8 | 3 | 12 | 5 | 3 |

TABLE 2

| Item 1 | Item 2 | Comparative Example 1 | Comparative Example 2 | Comparative Example 3 | Comparative Example 4 |
|---|---|---|---|---|---|
| Biodegradable Polymer Layer | Polymer | PLA-1 | — | PLA-1 | PLA-1 |
| | Thickness (nm) | 150 | — | 150 | 2000 |
| First Layer | Polymer | Pullulan-1 | Pullulan-1 | Pullulan-1 | Pullulan-1 |
| | Thickness (μm) | 5 | 5 | 5 | 5 |
| Fabric Structure | Designation | Reference Example 1 | Reference Example 1 | Reference Example 10 | Reference Example 1 |
| | Polymer | Pullulan-1 | Pullulan-1 | Pullulan-1 | Pullulan-1 |
| | Fabric Diameter (μm) | 5 | 5 | 0.0001 | 5 |
| | Thickness (μm) | 300 | 300 | 50 | 300 |
| Second Layer | Polymer | Pullulan-1 | Pullulan-1 | — | Pullulan-1 |
| | Thickness (μm) | 25 | 5 | — | 5 |
| Further Layer | Polymer | — | — | — | — |
| | Thickness (μm) | — | — | — | — |

TABLE 2-continued

| Item 1 | | Comparative Example 5 | Comparative Example 6 | Comparative Example 7 | Comparative Example 8 | Comparative Example 9 |
|---|---|---|---|---|---|---|
| Biodegradable Polymer Layer | | — — | — — | PLA-3 — | PLA-1 500 | PLA-1 150 |
| First Layer | | — — | Pullulan-1 5 | — — | Pullulan-1 5 | — — |
| Fabric Structure | | Reference Example 11 Pullulan-1 200 1,000 | Reference Example 12 Gelatin-1 100 2,000 | — — — — | Reference Example 1 Pullulan-1 5 300 | Reference Example 13 PVA-2 50 15,000 |
| Second Layer | | — — | Pullulan-1 5 | — — | Pullulan-1 5 | — — |
| Further Layer | | — — | — — | — — | PLA-1 500 | — — |

TABLE 3

| | Example 1 | Example 2 | Example 3 | Example 4 | Example 5 | Example 6 | Example 7 | Example 8 | Example 9 | Example 10 | Example 11 | Example 12 |
|---|---|---|---|---|---|---|---|---|---|---|---|---|
| Piercing Strength | A | A | B | A | A | A | B | A | B | A | A | A |
| Trocar Passing Characteristic Dry | A | A | B | A | A | A | B | A | A | A | A | B |
| Trocar Passing Characteristic Wet | A | A | B | A | A | A | A | A | B | A | A | B |
| Adhesiveness | A | A | A | A | A | A | A | A | A | A | A | A |
| Solubility | A | A | B | A | A | A | B | A | B | A | A | B |

TABLE 4

| | Comparative Example 1 | Comparative Example 2 | Comparative Example 3 | Comparative Example 4 | Comparative Example 5 | Comparative Example 6 | Comparative Example 7 | Comparative Example 8 | Comparative Example 9 |
|---|---|---|---|---|---|---|---|---|---|
| Piercing Strength | A | A | — | A | C | A | — | A | C |
| Trocar Passing Characteristic Dry | C | A | — | A | B | B | — | A | A |
| Trocar Passing Characteristic Wet | C | C | — | A | C | C | — | A | B |
| Adhesiveness | A | — | — | C | — | — | — | — | C |
| Solubility | A | A | — | A | A | C | — | C | C |

As shown in Tables 3 and 4, the evaluations of piercing strength, trocar passing characteristic, adhesiveness, and solubility were good in Examples 1 to 12. Comparative Examples 1 to 2 and 4 to 6 were defective with reference to at least one of the items. The noteworthy points will be described below.

With regard to trocar passing characteristic, the second film in Comparative Example 1 had a thickness of 25 µm, which was too thick, and thus the film exhibited much stiffness, failed to have a folded structure suitably fitted in a trocar, was broken, and failed to pass through the trocar whether it was dry or wet, resulting in B rating. In Comparative Examples 2, 5, and 6, each test piece successfully passed through the trocar when it was dry, but because each side of the laminate was a film or a fabric structure containing a water-soluble polymer, the test piece was broken by the swelling of the water-soluble polymer when there was moisture in the trocar, and failed to pass therethrough, resulting in B rating.

With regard to adhesiveness, the second film containing the water-soluble polymer in Comparative Example 1 had a thickness of 25 µm, which was too thick, and the fabric structure containing the water-soluble polymer in Comparative Example 9 had a thickness of 15,000 µm, which was too thick, and because of this, the water-soluble material layer was not removed sufficiently, and the test piece was rated B in terms of adhesiveness. In Comparative Example 4, the biodegradable material layer had a thickness of 2,000 nm, which was too thick, and because of this, the adherent force was insufficient and caused slippage to the adherend, and hence the test piece was rated B. In Comparative Examples 2, 5, and 6, each whole laminate was formed of a water-soluble material, because of which it was swollen, resulting in B rating in terms of adhesiveness.

With regard to solubility, the test piece in Comparative Example 5 dissolved instantly, and hence resulted in a B rating. In Comparative Examples 6, 7, and 8, each fabric structure portion did not dissolve even when five minutes elapsed after water dropping, resulting in a B rating. In Comparative Example 7 among these, the biodegradable material layer formed of PLA was the layer on which water was dropped, because of which water drops remained on the surface, and hence the water-soluble polymer was not successfully removed, failing in adhesiveness evaluation.

INDUSTRIAL APPLICABILITY

The laminate can be suitably used particularly for medical supplies such as wound dressings and adhesion prevention materials and for external materials for skin such as skin care products and adhesive bandages.

The invention claimed is:

1. A laminate comprising:
    a 10 to 500 nm thick biodegradable material layer containing an aliphatic polyester and a water-soluble material layer disposed on a first side of the biodegradable material layer,
    wherein the water-soluble material layer is constituted of a 1 to 20 μm thick first film containing a water-soluble polymer (a) and a 10 μm to 10 mm thick fabric structure containing a water-soluble polymer (b), which are layered in this order from the biodegradable material layer side, and
    a 1 to 20 μm thick second film containing a water-soluble polymer (c) disposed on a second side of the biodegradable material layer,
    wherein the water-soluble polymer (c) is pullulan,
    the aliphatic polyester is copolymerized polylactic acid polymer containing a lactic acid component and a copolymerizable monomer component,
    the copolymerizable monomer component is selected from the group consisting of hydroxycarboxylic acids, compounds containing a plurality of hydroxyl groups in the molecule or derivatives thereof and compounds containing a plurality of carboxylic groups in the molecule or derivatives thereof, and
    the copolymerizable monomer component has a 40 mol % or less content with respect to 100 mol % of all monomer components constituting the copolymerized polylactic acid polymer.

2. The laminate according to claim 1, wherein the laminate is such that 5 seconds or more but less than 5 minutes is required from the time when water is dropped onto the surface of the second film to the time when the surface of the first film is dissolved, wherein the surface of the first film is in contact with the biodegradable material layer.

3. The laminate according to claim 1, wherein the biodegradable material layer has a thickness of 10 to 200 nm.

4. The laminate according to claim 1, wherein the first film has a thickness of 2 to 10 μm.

5. The laminate according to claim 1, wherein the second film has a thickness of 5 to 20 μm.

6. The laminate according to claim 1, wherein the fabric structure has a thickness of 100 μm to 1 mm.

7. The laminate according to claim 1, wherein the water-soluble polymer (a) is pullulan or polyvinyl alcohol.

8. The laminate according to claim 1, wherein the water-soluble polymer (b) is pullulan or polyvinyl alcohol.

9. The laminate according to claim 1, wherein the water-soluble polymer (c) is pullulan or polyvinyl alcohol.

* * * * *